United States Patent [19]
Parker et al.

[11] Patent Number: 5,981,288
[45] Date of Patent: Nov. 9, 1999

[54] METHODS FOR DETERMINING THE CONCENTRATION OF SURFACTANTS IN HYDROCARBONS

[75] Inventors: Wiley L. Parker, Conroe; Alan E. Goliaszewski, The Woodlands; Nancy R. Calvert, Kingwood, all of Tex.

[73] Assignee: BetzDearborn Inc., Trevose, Pa.

[21] Appl. No.: 08/949,318

[22] Filed: Oct. 14, 1997

[51] Int. Cl.$^6$ .................................................. G01N 33/00
[52] U.S. Cl. ........................... 436/104; 436/60; 436/111; 436/120; 436/128; 436/129; 436/131; 436/166; 436/177; 436/183
[58] Field of Search .............................. 436/60, 104, 128, 436/131, 166, 175, 177, 183, 111, 120, 129

[56] References Cited

U.S. PATENT DOCUMENTS

| | | | |
|---|---|---|---|
| 3,321,399 | 5/1967 | Versteeg et al. | 508/356 |
| 3,913,385 | 10/1975 | Jobe | 73/64.4 X |
| 5,596,130 | 1/1997 | Wright et al. | 585/3 |
| 5,621,154 | 4/1997 | Wright et al. | 585/3 |
| 5,721,143 | 2/1998 | Smith et al. | 436/163 |

FOREIGN PATENT DOCUMENTS 6-304468  11/1994  Japan .

OTHER PUBLICATIONS

R. Davies et al. In "Proc. Tech. Program: Int. Powder Bulk Solids Handl, Process" 1978, pp. 231–238, Ind. Sci. Conference Manage., Inc,: Chicago, Ill. Sargent–Welch Catalog 1984, pp. 1463, 1587+1770–1824.

A.A.Nigmad'yanov et al. *Metody Anal. Kontrolya Kach Prod. Khim. Prom.–Sti.* 1978, 62–65.

D.L. Kuehne et al. *Society of Petroleum Engineers Journal* 1985, 25, 687–692.

N. Buschmann *Fresenius Z. Anal. Chem.* 1987, 326, 123–126. S. Dasgupta *J. Colloid Interface Sci.* 1988, 124, 22–27.

S. Dasgupta *J. Colloid Interface Sci.* 1988, 124, 22–27.

K. Esumi et al. *Colloids Surf.* 1988, 32, 139–147.

Grafton, "Beer Hazes", Oct. 9, 1995, http://sun1.bham.ac.uk/GraftonG/haze.htm.

New Scientific Company–Cormano (Milano), Nephelometry, Turbidimetry Kits, http://web.tin.it.nsc/inglese.htm, 1997.

New Scientific Company–Cormano(Milano), Free Light Chains–Presentation, http://web.tin.it.nsc/inglese.htm, 1997.

*Primary Examiner*—Arlen Soderquist
*Attorney, Agent, or Firm*—Philip H. Von Neida

[57] ABSTRACT

The present invention provides for a method and system for determining the concentration of a surfactant in a transparent hydrocarbon by performing the steps of adding a solid to the hydrocarbon; adding a second masking reagent to the hydrocarbon; mixing to form a dispersion; separating the dispersion from the mixture; and measuring the optical absorption of the dispersion.

10 Claims, No Drawings

METHODS FOR DETERMINING THE CONCENTRATION OF SURFACTANTS IN HYDROCARBONS

FIELD OF THE INVENTION

The present invention relates to analytical methods for determining the concentration of surfactants in hydrocarbons. More particularly, the present invention provides analytical methods for determining the concentration of dispersants in transparent hydrocarbons, such as jet fuels.

BACKGROUND OF THE INVENTION

Hydrocarbons are susceptible to chemical reactions due to aging, heat and oxidation. One effect of oxidation, for example, is to produce soluble and insoluble materials of higher molecular weight and boiling point than the original hydrocarbon. These materials can have deleterious effects on the ultimate use of the hydrocarbons.

In particular, turbine combustion fuel oils, such as JP-4, JP-5, JP-7, JP-8, Jet A, Jet A-1, and Jet B are subject to harsh conditions. Fuel burned in an aircraft engine is often used as a cooling medium or heat sink to cool aircraft subsystems and engine lubricating systems prior to its combustion. As the fuel passes through the heat exchangers, it is subjected to temperature increases of several hundred degrees in a matter of seconds. Any unstable constituents in the fuel will quickly react under these severe conditions forming gums, varnishes and coke deposits. These deposits will plug-up the components leading to operational problems including reduced thrust and performance anomalies.

Treatment of these problems in hydrocarbons has often been accomplished with additives such as antioxidants, metal deactivators and corrosion inhibitors. Surfactants in the form of dispersants are often added to assist in retarding fouling of the hydrocarbons. However, hydrocarbons contain a number of naturally occurring dispersants as well as those of the additive variety. Consequently, this makes analytical determination of any one dispersant present in the hydrocarbon difficult due to contributions from the other dispersants present. The present inventors have surprisingly discovered an analytical method for determining the concentration of selected dispersants in transparent hydrocarbon fuel that avoids interferences from other dispersants present in the hydrocarbon.

Analytical tests based on turbidity measurement are often encountered in clinical chemistry and molecular biology laboratories. In these tests, turbidity measurement is used as a means of detecting and quantifying the concentration of a species which is made to precipitate from solution or absorb onto dispersed latex particles. A related analytical method utilizes turbidity measurements to detect suspended solids. Nephelometry is a photometric analytical technique for measuring the light scattered by finely divided particles of a substance in suspension. These techniques are used in industries as diverse as brewing and smart appliance manufacture (e.g., washing machines). The focus application of the turbidity measurement in these examples is to quantitate the solids present in the fluid, not to quantitate the concentration of dispersant in the fluid. However, none of these techniques account for methods to counteract the interference of other dispersants in the tested fluids.

DETAILED DESCRIPTION OF THE INVENTION

The present invention relates to methods for determining the concentration of a surfactant in a transparent hydrocarbon comprising the steps of:

a) adding an effective amount of solid which is effective for the purpose to the transparent hydrocarbon containing the surfactant;

b) adding an effective amount to the hydrocarbon of a second reagent effective for the purpose of counteracting interferences from surfactants other than that which is being analyzed for;

c) mixing the solid, second reagent and the transparent hydrocarbon to form a dispersion;

d) separating the dispersion from the mixture; and e) measuring the optical absorption of the dispersion to determine the level of surfactant in a hydrocarbon.

The present invention also relates to a system for determining the concentration of a surfactant in a transparent hydrocarbon, said system comprising:

a) addition means for adding an effective amount of a solid which is effective for the purpose to said transparent hydrocarbon containing the surfactant;

b) addition means for adding an effective amount to the hydrocarbon of a second reagent effective for the purpose of counteracting interferences from surfactants other than that which is being analyzed for;

c) mixing means for mixing the solid, the second reagent and the transparent hydrocarbon to form a dispersion;

d) separation means for separating the dispersion from the mixture; and e) measuring means for measuring the optical absorption of the dispersion to determine the level of said surfactant in said hydrocarbon.

The surfactants that can be detected by the methods of the present invention are preferably dispersants that are used in hydrocarbons. The present inventors believe that these surfactants include but are not limited to compounds of the general formula R-X where R is a $C_{10}$ to $C_{200}$, preferably $C_{50}$ to $C_{100}$ polymeric hydrocarbon end obtained by the polymerization of α-olefins such as ethylene, propylene and isobutylene. X represents a polar end selected from the group consisting of amides and imides, amines, esters, ethers, carboxylic acids, phenols, alcohols, phosphorous, boron and sulfur compound, and metal salts.

The surfactants preferably include but are not limited to polyisobutylene thiophosphonate esters, such as those described in U.S. Pat. Nos. 5,596,130 and 5,621,154, the contents of which are wholly incorporated by reference to herein and derivatives of polyalkylenesuccinic anhydrides (PIBSA).

The solids that are employed in the present invention include but are not limited to metal oxides, with iron oxide ($Fe_2O_3$) most preferred. The solid is preferably added to the transparent hydrocarbon/reagent combination in an amount ranging from about 0.75 mg/ml to about 16.00 mg/ml.

The transparent hydrocarbons are defined as those hydrocarbons for which optical absorption measurements can be taken. These hydrocarbons include but are not limited to naphtha, gasoline, kerosene, diesel fuel, jet fuel, turbine combustion fuel oils, gas oils, vacuum residuals, etc.

Typically, the transparent hydrocarbon containing surfactants is treated with the solid material. The second reagent is added to the hydrocarbon. The second reagent may be defined as a chemical reagent or reagents that masks or modifies the action of surfactants present in the hydrocarbon other than the one being tested for. Consequently, there is little or no competition for the solid material between this desired surfactant and the largely extraneous ones.

Examples of this reagent include but are not limited to ketones such as acetone, methyl ethyl ketone (MEK) and butyl ketone. This second reagent is added in an amount which is sufficient to mask the action of the other surfactants. Preferably this ranges from about 0.1 to about 2.0 ml per ml of hydrocarbon.

This whole mixture of transparent hydrocarbon, solid material and second reagent is gently mixed by repeated inversion to create a dispersion. This dispersion is subsequently centrifuged so that the desired surfactant dispersion is separated from the mixture of hydrocarbon and other poorly dispersed surfactants.

The resulting dispersion is then measured using an appropriate colorimeter to determine the concentration of the desired surfactant in the hydrocarbon.

The advantages of this test method are that it is relatively inexpensive both in materials and in performance. The method can be performed on-site and in the field and does not require an analytical laboratory. The test is relatively rapid and requires little specially constructed equipment and no extensive operator training.

In order to more clearly illustrate this invention, the data set forth below were developed. The following examples are included as illustrations of the invention and should not be construed as limiting the scope thereof.

EXAMPLE

Six round bottom 13 ml culture tubes with 0.1015 g to 0.1034 g of raw Fisher $Fe_2O_3$ were prepared. 8.00 ml of acetone was added to each tube. 5 ml of Jet A jet fuel containing various concentrations of the thermal stability additive was added to each tube. For JP 8 and JP 5 specification fuels, the protocol calls for 2.0 ml of acetone to 10.0 ml of jet fuel.

The entire set of six tubes was capped and inverted approximately two times per five seconds for five minutes. The tubes were then centrifuged on a Fisher Scientific Centrific Model for five minutes at a speed of 850 rpm.

The tubes were removed from the centrifuge and about 8.00 ml was pipetted from the tubes into French square bottles. A Hach Colorimeter with a fixed wavelength of 528 nm was zeroed using 10 ml of kerosene in a 10 ml cell. The contents of the sample were then poured into the cleaned cell and the optical absorption for each sample was measured.

Testing was performed for a powerful dispersant, a derivative of polyalkenylthiophosphonic acid as described in the U.S. Pat. No. 5,621,154 in turbine combustion fuel oils. These fuels oils were of military specification as per use in military aircraft.

Concentration of the surfactant was determined through linear regression analysis. The results of this testing are presented in Tables I, II and III.

TABLE I

Linear regression analysis equations for different fuel specifications.

JP5
Concentration (ppm actives) = (colorimeter counts − 174)/43.5
JP8
Concentration (ppm actives) = (colorimeter counts − 193)/40.35
Jet A
Concentration (ppm actives) = (Colorimeter counts − 56)/7.73

TABLE II

| Concentration | Colorimeter Counts | | | |
|---|---|---|---|---|
| Surfactant (in ppm) | JP5 (1st Run) | JP5 (2nd Run) | JP5 (Avg.) | JP8 |
| 0 | 159 | 170 | 164.5 | 182 |
| 2.5 | 245 | 223 | 234 | 277 |
| 5.0 | 397 | 354 | 375.5 | 405 |
| 10.0 | 730 | 743 | 736.5 | 630 |
| 20.0 | 990 | 990 | 990 | 982 |

JP5 and JP8 fuel response in residual test.

For JP 8 and JP 5 fuels, 2.0 ml of acetone to 10.0 ml jet fuel was used in the test. The test results were erratic when 8.0 ml of acetone to 5.0 ml jet fuel was employed.

TABLE III

| Concentration of Surfactant (in ppm) | Fuel 2827* | Fuel 2926* | Fuel 3084* | Fuel 3119* |
|---|---|---|---|---|
| 0 | 29 | 25 | 62 | 76 |
| 1.0 | 48 | 63 | 62 | 53 |
| 2.5 | 70 | 45 | 104 | 108 |
| 5.086 | 82 | 113 | 124 | |
| 10.0 | 125 | 132 | 171 | 148 |
| 20.0 | 194 | 144 | 241 | 236 |

Jet A fuel response in residual test.
*Specification of various sources of base fuel.

Additional testing was performed in both a hot box and outdoors to determine the effects of humidity and temperature on the analytical method. The results of this testing are reported in Table IV.

TABLE IV

| Concentration of Surfactant (in ppm) | 92° F. ~60% humidity | 102° F. ~60% humidity | 99.5° F. ~88% humidity | Lab avg. 76° F. ~70% humidity | 30° F. |
|---|---|---|---|---|---|
| 0 | 220 | 200 | 161 | 182 | 113 |
| 25 | 358 | 375 | 162 | 277 | 179 |
| 50 | 547 | 531 | 140 | 405 | 263 |
| 100 | 748 | 690 | | 630 | 460 |
| 200 | 990 | 990 | | 983 | 612 |

JP8 Fuel Response in Residual Test

These results indicate that changes in the relative amounts of humidity and temperature will have an effect on the analytical method results. The inventors believe that the humidity increases the amount of water in the sample which increases the competition for the surfactant. As temperature increases, the colorimeter count increases possibly due to increased molecular activity.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A method for determining the concentration of a surfactant selected from the group consisting of amides, imides, amines, esters, carboxylic acids, phenols, alcohols, phosphorous, boron, sulfur compounds and metal salts, in a transparent hydrocarbon comprising the steps of:
    a) adding an effective amount of a solid selected from the group consisting of metal oxides to said transparent hydrocarbon containing said surfactant;
    b) adding an effective amount of a second reagent selected from the group consisting of acetone, methyl ethyl ketone and butyl ketone effective for the purpose of masking to said transparent hydrocarbon;
    c) mixing the solid, second reagent and the transparent hydrocarbon to form a dispersion;
    d) separating the dispersion from the mixture; and
    e) measuring the optical absorption of the dispersion to determine the level of said surfactant in said hydrocarbon.

2. The method as claimed in claim 1 wherein said solid is iron oxide.

3. The method as claimed in claim 1 wherein said transparent hydrocarbon is selected from the group consisting of naphtha, gasoline, kerosene, diesel fuel, jet fuel, turbine combustion fuel oils, gas oils, and vacuum residuals.

4. The method as claimed in claim 3 wherein said transparent hydrocarbon is selected from the group consisting of turbine combustion fuel oils and jet fuel.

5. The method as claimed in claim 1 wherein said second reagent is acetone.

6. The method as claimed in claim 1 wherein said solid is added to said transparent hydrocarbon in an amount ranging from about 0.75 mg per ml to about 16.00 mg solid per ml of hydrocarbon.

7. The method as claimed in claim 1 wherein said second reagent is added to said hydrocarbon in an amount ranging from about 0.1 ml to about 2.0 ml per ml of hydrocarbon.

8. The method as claimed in claim 1 wherein said separation is by a centrifuge.

9. The method as claimed in claim 1 wherein said optical absorption is measured with a colorimeter.

10. A method for determining the concentration of polyisobutylene thiophosphonate ester in a jet fuel comprising the steps of:
    a) adding an effective amount of iron oxide to said jet fuel containing said polyisobutylene thiophosphonate ester;
    b) adding an effective amount of acetone to said jet fuel;
    c) mixing said iron oxide, acetone and jet fuel to form a dispersion;
    d) separating the dispersion from the mixture; and
    e) measuring the optical absorption or the dispersion to determine the concentration of said polyisobutylene thiophosphonate ester in said jet fuel.

* * * * *